United States Patent
LaDuca

(12) 
(10) Patent No.: US 6,248,547 B1
(45) Date of Patent: Jun. 19, 2001

(54) REAGENT COCKTAIL PREPARATION FOR THE RAPID PRODUCTION OF SERUM

(75) Inventor: Frank M. LaDuca, East Brunswick, NJ (US)

(73) Assignee: International Technidyne Corp., Edison, NJ (US)

( * ) Notice: Subject to any disclaimer, the term of this patent is extended or adjusted under 35 U.S.C. 154(b) by 0 days.

(21) Appl. No.: 08/169,968

(22) Filed: Dec. 17, 1993

Related U.S. Application Data

(63) Continuation of application No. 07/978,190, filed on Nov. 18, 1992, now abandoned, which is a continuation of application No. 07/758,741, filed on Sep. 12, 1991, now abandoned, which is a division of application No. 07/583,164, filed on Sep. 17, 1990, now Pat. No. 5,089,415.

(51) Int. Cl.$^7$ ..................................................... C12R 1/56
(52) U.S. Cl. .............................................................. 435/13
(58) Field of Search .................................. 435/2, 13, 269

(56) References Cited

FOREIGN PATENT DOCUMENTS 58-01460 * 1/1983 (JP) ................................. A61M/1/03
61-53567 * 3/1986 (JP) ................................. G01N/33/48

OTHER PUBLICATIONS

Bezeaud et al., Prothrombin Salakta: An Abnormal Prothrombin Characterized By a Defect In the Active Site of Thrombin, Thrombosis Research vol. 34, pp. 507–518 (1984).
S. Thomas Shaw, Jr., "Assays For Fibrinogen And Its Derivatives," CRC Critical Reviews In Clinical Labratory Sciences, vol. 8 , No. 2. (Oct. 1977).
Bell, William R., "Defribrinogenating Enzymes," Hemostosis and Thrombosis: Basic Principles and Clinical Practice, Chapt. 54, Edited by J.P. Lippercott (1987).
Sigria Catalog, p. 188 (1985).*
Grant & Hackh's Chemical Dictionary p. 526, 1989.*
J. Lewis et al, Blood 51:129–137 (1978).*

* cited by examiner

*Primary Examiner*—Sandra E. Saucher
(74) *Attorney, Agent, or Firm*—Arthur L. Plevy, Esq.; Duane, Morris & Heckscher, LLP

(57) ABSTRACT

A cocktail reagent preparation for the rapid production of serum contains thrombin, snake venom, and protamine sulfate. The preparation employs very small quantities of clot promoting substances which behave in a synergistic manner such that rapid clotting of highly heparinized blood is achieved without altering the chemical analysis of the blood enzymes, proteins, sugars, or electrolytes. Thus, clinicians who rely upon the results of such tests can more closely monitor organ and tissue function and adjust patient therapies accordingly.

24 Claims, No Drawings

REAGENT COCKTAIL PREPARATION FOR THE RAPID PRODUCTION OF SERUM

This is a continuation of application Ser. No. 07/978,190, filed on Nov. 18, 1992 now abandoned, entitled Reagent Cocktail Preparation for the Rapid Production of Serum which is a continuation of Ser. No. 07/758,741 now abandoned filed on Sep. 12. 1991 which is a divisional of Ser. No. 07/583,164 filed on Sep. 17, 1990 and now U.S. Pat. No. 5,089,415.

FIELD OF THE INVENTION

The present invention relates, in general, to the production of serum, and, more particularly to a reagent preparation for the rapid production of a high quality serum specimen upon which diagnostic blood chemical analyses can be performed.

BACKGROUND OF THE INVENTION

Serum represents the liquid portion of the blood which remains following the clotting of the formed blood elements and blood coagulation factors. The serum contains various blood proteins, sugars, fats, enzymes and charged particles (i.e., electrolytes) which are necessary for normal metabolic processes. Devoid from the serum are the elements consumed during the clotting process namely red blood cells, white blood cells, platelets and the blood coagulation factors. Serum, obtained by centrifugation of clotted blood, is used to conduct chemical analyses which are valuable tests used to diagnose and monitor muscle and organ function, metabolic balances, and basic physiologic functions. By removing the substances consumed during clotting, a better substrate upon which to perform chemical analyses is produced. Thus, serum is the preferential test substrate on which to perform analytical tests such as enzyme, electrolyte, protein and glucose assays since the interference of unwanted substances has been removed. These analytical tests are routinely performed using automated chemistry analyzers such as the Hitachi 717, Technicon SMAC, and Ciba-Corning 5500 Express.

In the past, the production of serum from whole blood has been a passive process in which freshly collected blood is added to a glass test tube and allowed to clot. Blood, once removed from the body, has a natural tendency to clot and its exposure to a surface such as glass promotes clotting in a more efficient manner. Contact with a glass surface causes the activation of coagulation factors which interact in a mechanism commonly referred to as the coagulation cascade. In this process, an inactive coagulation factor is chemically converted to an active enzyme which subsequently converts yet another inactive precursor. The coagulation factors are identified by Roman Numerals; Factors I–XIII. The end result of the coagulation cascade is a conversion of the soluble plasma protein fibrinogen, to an insoluble protein, fibrin, whereby the fibrin clot entraps the white cells, red cells, and platelets forming a solid gelatinous mass. Substances not consumed in the process remain free of the gelatinous mass and are found in the liquid matrix. It is this liquid portion which serves as the best test substrate upon which to perform serum chemistry analyses.

The passive clotting process described above has several inadequacies. Blood from normal healthy individuals will routinely clot in approximately 6 to 10 minutes in a glass test tube. However, blood from sick individuals who may have deficiencies of coagulation proteins or from patients who are receiving anticoagulation therapy (i.e., oral anticoagulants or heparin) may require extensive time to clot (i.e., 2–8 hours). Typically highly heparinized blood is between 2–5 units per milliliter and possibly higher. Consequently, in the past, there has been a delay associated with the obtaining of blood specimens and the performance of the analytical tests, thereby affecting the ability of the clinician to quickly provide optimal patient care. In addition, the blood from individuals with deficiencies of coagulation proteins or patients receiving anticoagulation therapy may never form a complete and adequate fibrin mass. Incomplete clotting in heparinized blood specimens results in a poor quality serum substrate upon which to perform the chemical test. Furthermore, heparin anticoagulated blood which may not clot initially may actually begin to clot once placed in the chemistry analyzer, thereby clogging the system and causing an instrument shutdown.

In order to improve the clot forming process, laboratorians have routinely added the clot promoting agent thrombin to the blood specimen. Thrombin actively converts fibrinogen to fibrin, thereby forming the clot more efficiently then the slower glass-activated clotting process. Although thrombin may improve clotting in normal blood, it's effects on heparinized blood are minimal since heparin acts as an inhibitor of thrombin. As a result, collection of heparinized blood in these thrombin containing serum test tubes provides little improvement of the serum specimens, both in quality as well as in the time required to prepare the specimens, as compared to the plain glass test tube. Thrombin containing test tubes are available from Becton-Dickinson and Company, VACUTAINER Systems, of Rutherford, N.J. 07070. Though it is possible to overcome the anticoagulant effect of heparin with very large amounts of thrombin, the fibrin mass so formed is often an incomplete one. Consequently, following the centrifugation of an apparently clotted specimen, delayed clotting occurs in the serum supernatant rendering it of little use in analytical tests. Moreover, such an excessive thrombin quantity will interfere with the proper performance of the chemical analyses, thereby altering the test results. Furthermore, excessive procoagulants such as thrombin can cause some red blood cell hemolysis, whereby the red blood cell bursts open contaminating the serum specimen with intracellular particles. The above stated problems relating to the rapid production of a high quality serum specimen from heparinized patients on which to perform chemical analyses are significant since many patients receiving heparin anticoagulation therapy require repetitive serum chemistry analyses.

SUMMARY OF THE INVENTION

The problems and disadvantages associated with the prior art methods of obtaining serum discussed above are overcome in accordance with the present invention by providing a cocktail preparation to enable relatively rapid clotting of highly heparinized blood when the preparation is mixed with a given volume of blood. The preparation contains thrombin, a heparin neutralizing substance, and a snake venom which is capable of converting fibrinogen to fibrin and is unaffected by the presence of heparin. The thrombin, heparin neutralizing substance, and snake venom are present in the preparation in sufficient amounts to rapidly clot the highly heparinized blood sample to enable the serum to be separated from the clotted matter. The serum is then chemically tested is to provide clinically accurate blood chemistry results.

By providing such a clot promoting cocktail, it is now possible to prepare serum specimens and obtain accurate blood chemistry analyses of highly heparinized patients in a rapid fashion. Clinicians who rely upon results of such tests to monitor and adjust patient therapies now have the means to more closely identify patient deficiencies and provide the appropriate treatment. Thus, the patient benefits from a more closely monitored therapeutic regimen.

DETAILED DESCRIPTION OF THE EXEMPLARY EMBODIMENTS

The present invention describes a unique combination of clot promoting reagents which when combined with fresh normal blood, fresh blood from coagulation deficient patients, or fresh blood from heparinized patients results in rapid clotting of the blood. By applying this reagent combination in very low concentration it is possible to clot non anticoagulated blood from normal individuals within two minutes and blood from patients receiving heparin therapy within five minutes. Prior to the development of this clot promoting preparation, non anticoagulated blood required three to five times as long to clot (i.e., 6–10 minutes) and heparinized blood would not clot for several hours. Some heparinized blood samples actually remained non-coagulated after 6–8 hours.

The reagents used to formulate the cocktail include two clot promoting enzymes, thrombin and snake venom, and a heparin neutralizing reagent, protamine sulfate. Thrombin may be obtained from the plasma of several animal species including, but not limited to, cows (i.e., bovine), sheep, horse, pig, rat, mouse, and humans. In the preferred embodiment, thrombin from a bovine source is used. The snake venoms may be derived from one of several species of snakes which convert fibrinogen to fibrin and are unaffected by the presence of heparin, including, but not limited to the family of snakes known as the Genus: Agkistrodon, Bothrops, Crotalus, Eschis, and Trimeresurus. In the preferred embodiment, the venom from the snake *Bothrops atrox*, or alternately, the purified procoagulant portion of the crude venom, atroxin, is used. It is understood that the clot promoting effect requires the conversion of fibrinogen to fibrin while being unaffected by heparin. Hence, it is possible that recombinant forms of snake venom might be employed. The protamine sulfate is extracted from fish of the species salmon. Protamine sulfate is preferred, but protamine chloride (salmon) can be used as well. Essentially any heparin neutralizing preparation can be employed such as polybrene, heparinase, and anion exchange resins such as TEAE cellulose, DEAE cellulose providing that the blood chemistry is not significantly altered.

The reagent preparation is prepared by combining individual reagents into a common batch. Appropriate stabilizers and buffers are added to insure an acceptable shelf life. The combination of reagents may be used in liquid form or alternatively may be freeze-dried using the basic principals of lyophilization. The liquid or dried powered reagent may then be added directly to a blood collection test tube, or alternatively, to a special centrifugation container. Either glass or plastic containers may be used.

To prepare the reagent cocktail, individual stock reagents are assembled, rehydrated if required, and allowed to stabilize. In a first container, bovine thrombin is dissolved in barbital buffered saline (i.e., hereinafter "BBS"), to a final concentration of 100 USP units per milliliter (equivalent to approximately 1 mg/ml); the BBS is commercially available from Sigma Chemical Co. St. Louis, Mo. Bovine thrombin, commercially available from many sources, is easy to prepare and relatively inexpensive. Crude snake venom extract from the snake *Bothrops atrox* is dissolved in BBS to a concentration of 1 mg/ml in a second container. Then, in a third container, protamine sulfate (from salmon) is dissolved in a sodium chloride (NaCl) solution to a concentration of 10 mg/ml. A preservative such as thimerosal or sodium azide may also be added at a final concentration of 0.02% to each individual container. The reagents are combined into a cocktail preparation such that the final concentration in blood is 0.5 units of thrombin per ml, 0.01 mg of snake venom per ml and 0.05 mg of protamine per ml. The reagents are in sufficient concentration such that a small amount of this "cocktail" reagent is required to clot a blood specimen. This eliminates the possibility of a dilution effect creating false chemistry analyses. If the addition of the cocktail results in a dilution of the original blood volume by about 5% or more, this may render the final serum sample clinically unacceptable.

If the volume of blood to be clotted is 3 ml, a total of 0.04 ml of the cocktail reagent is prepared consisting of 0.015 ml of the thrombin solution from the first container, 0.01 ml of the snake venom solution from the second container, and 0.015 ml of the protamine sulfate solution from the third container. Stock reagent preparations of greater or lesser concentration may also be employed and final quantities in the cocktail adjusted to achieve the desired preferred concentration. The volume 3 ml was selected as an example due to the fact that compact centrifuges employ 3 ml as a typical load. Alternatively, we may collect a 6 ml blood sample by adding 0.08 ml of the reagent cocktail to the blood or a 9 ml blood sample by adding 0.120 ml of the cocktail, and so on. Preferred and acceptable formulations are as follows:

| Formulaton of the Reagent Preparation | | |
|---|---|---|
| Component Reagent | Preferred Concentration* (per milliliter) | Range of acceptable conc. (per millimeter) |
| Thrombin | 0.5 units | 0.2–3.0 units |
| Snake Venom | 0.0033 mg | 0.002–0.20 mg |
| Protamine Sulfate | 0.05 mg | 0.02–0.08 mg |
| BBS comprising | | |
| sodium barbital | 1.17 mg | 0.39–2.34 mg |
| sodium chloride | 1.46 mg | 0.48–2.92 mg |
| sodium azide** | 0.5 mg | 0–1.0 mg |
| thimerosal** | 0.2 mg | 0–0.5 mg |

*The preferred concentration is the one used in the current cocktail configuration and is the concentration of each component reagent as found in the blood sample. These concentrations remain constant irrespective of blood volume.
**Either sodium azide or thimerosal may be used as a preservative or another appropriate antibacterial agent used.

As indicated, the cocktail as described above may be in liquid form. This liquid may then be placed in a collection reservoir to which blood is subsequently added. Alternatively, the liquid cocktail may be placed in a collection reservoir, and the reservoir, either plastic or glass, may be freeze dried using conventional methods. A suitable freeze drying apparatus (i.e., a lyophilizer) is sold by the Virtus Company of Gardineer, NY and sold under the designation of Unitop 600. The lyophilizer removes the water molecules such that the various proteins and reagents remain in a dried (powdered) state. The freeze dried preparation may be stored in any suitable container and subsequently transferred to an appropriate blood collection receiver. In a preferred embodiment, the entire solution is freeze dried to the inside of the collection receiver. The collection reservoir may be one of several configurations depending upon the apparatus to be used for centrifugation, and for collection of the serum. The following examples illustrate suitable collection reservoirs and centrifugation systems of the reagent cocktail use.

EXAMPLE 1

The reagents as combined to form the cocktail preparation are added to a glass or plastic test tube or collection reservoir. The amount of the cocktail preparation added is a function of the size of the reservoir as indicated above (i.e., 0.04 ml for 3 ml of anticipated sample). The tube may be evacuated to a pre-determined amount and stoppered. The tube also serves as the blood collection reservoir as blood is added directly to the tube, mixed, and allowed to clot. The clotted specimen is then centrifuged in an appropriate centrifuge instrument and the serum removed for testing.

EXAMPLE 2

According to Example 1 above wherein the cocktail preparation is lyophilized in the test tube prior to evacuation and stoppering.

EXAMPLE 3

The cocktail preparation is placed in a small glass or plastic container and stoppered. To use, the preparation is transferred to any blood collection reservoir and blood is subsequently added. Alternatively, the cocktail preparation may be added to a container of previously collected blood.

EXAMPLE 4

As per Example 3 above wherein the cocktail preparation is lyophilized in the container. Prior to use, the preparation is rehydrated with distilled water in a volume equivalent to the original volume of the cocktail added.

When a patient's blood is added to the cocktail preparation, clotting rapidly occurs as a result of the following simultaneous reactions: First, thrombin immediately converts fibrinogen to fibrin, thereby forming the initial fibrin strands. Secondly, protamine sulfate neutralizes the anticoagulant effects of heparin if present in the blood. If heparin is absent from the blood, the protamine sulfate is in a sufficiently low concentration such that it does not affect the normal clotting process. Third, the procoagulant portion of the snake venom extract activates and cleaves the remaining fibrinogen molecules which are ineffectively activated by the thrombin initially added. Through this enzymatic cleavage, all remaining fibrinogen is converted to fibrin resulting in the formation of a solid gelatinous mass consisting of the consumed coagulation factors and the entrapped formed blood elements (i.e., the red blood cells, white blood cells and platelets).

The clotted sample may then be transferred to an appropriate centrifugation container and spun at a high speed such that the gelatinous mass is forced to the bottom of the collection reservoir or test tube and the liquid serum remains as a supernatant. This serum supernatant may then be withdrawn from the collection reservoir using an appropriate pipetting device and transferred to the analytical cell of the chemistry analyzer. Any chemistry test normally performed on a serum preparation may be performed on the serum preparation generated in the presence of the clot promoting cocktail since the combination of reagents employed in the cocktail does not alter the test results. The rapid availability of the serum preparation enables the clinician to formulate an appropriate clinical course of patient management by allowing the clinician to properly monitor organ and tissue function and to assess metabolic processes important to the health of the patient.

The advantages of this clot promoting cocktail are: the ability to completely clot highly heparinized blood in a very rapid manner (i.e., less than 5 minutes), the ability to generate a high quality serum preparation from which chemical analyses may be performed, and the unique use of synergistic effects of very low concentrations of reagents in the preparation such that they do not interfere with the chemistry analysis performed.

The most commonly used chemistry profile includes analysis of a group of serum chemistry tests. This profile includes: electrolytes such as sodium, potassium, chloride, and calcium; serum enzymes such as glutamic oxaloacetic transaminase (SGOT), gamma glutamyl transpeptidase (GGTP), lactic dehydrogenase (LDH), alkaline phosphatase (ALK), and creatine phosphokinase (CPK); and dissolved substances such as bilirubin, glucose, cholesterol, blood urea nitrogen (BUN), creatine, uric acid, albumin, and total protein.

In the example that follows, one aliquot of blood was allowed to clot passively in a glass test tube (control) and a second aliquot was clotted in a glass test tube using the clot promoting reagent cocktail (cocktail). In additional samples, heparin was also added before the clotting process was initiated. The chemistry profiles were obtained for all specimens. As shown below, the cocktail preparation did not statistically alter (t-test of matched means) the chemistry test results, which is of paramount importance. Furthermore, patients with abnormal blood chemistries (i.e., glucose or cholesterol levels) are accurately measured using the cocktail preparation.

| TEST | COCKTAIL | CONTROL |
|---|---|---|
| I. Non-heparinized blood | | |
| sodium | 143.8 ± 4.3 | 141.0 ± 6.1 |
| potassium | 4.1 ± 0.3 | 4.0 ± 0.3 |
| chloride | 107.4 ± 5.0 | 106.8 ± 6.3 |
| calcium | 9.3 ± 0.4 | 9.0 ± 0.6 |
| SGOT | 20.0 ± 5.0 | 21.3 ± 5.6 |
| GGPT | 20.0 ± 10.9 | 20.4 ± 10.7 |
| LDH | 145.4 ± 34.2 | 164.8 ± 38.6 |
| ALK | 79.1 ± 18.5 | 76.0 ± 18.2 |
| CPK | 114.0 ± 62.8 | 109.2 ± 60.3 |
| bilirubin | 0.65 ± 0.38 | 0.60 ± 0.31 |
| glucose | 87.2 ± 7.2 | 83.2 ± 10.2 |
| cholesterol | 184.0 ± 25.5 | 178.0 ± 26.7 |
| BUN | 13.5 ± 4.0 | 13.4 ± 3.9 |
| creatine | 1.06 ± 0.2 | 1.06 ± 0.2 |
| uric acid | 4.6 ± 1.1 | 4.6 ± 1.4 |
| albumin | 4.7 ± 0.3 | 4.7 ± 0.4 |
| total protein | 7.0 ± 0.6 | 6.8 ± 0.6 |
| II. Heparinized blood | | |
| sodium | 143.7 ± 4.0 | 141.9 ± 7.0 |
| potassium | 3.6 ± 0.3 | 3.5 ± 0.3 |
| chloride | 110.0 ± 5.0 | 109.1 ± 6.8 |
| calcium | 8.3 ± 0.5 | 8.1 ± 0.7 |
| SGOT | 17.7 ± 4.2 | 16.9 ± 4.1 |
| GGPT | 19.9 ± 10.8 | 16.4 ± 9.1 |
| LDH | 135.9 ± 24.7 | 129.4 ± 24.8 |
| ALK | 73.2 ± 18.1 | 70.7 ± 14.6 |
| CPK | 87.0 ± 50.0 | 85.6 ± 48.0 |
| bilirubin | 0.63 ± 0.34 | 0.57 ± 0.30 |
| glucose | 83.8 ± 7.8 | 79.8 ± 10.9 |
| cholesterol | 161.1 ± 14.2 | 156.9 ± 21.9 |
| BUN | 12.1 ± 3.6 | 11.9 ± 3.7 |
| creatine | 0.9 ± 0.2 | 1.0 ± 0.2 |
| uric acid | 4.1 ± 0.8 | 4.1 ± 0.8 |
| albumin | 4.3 ± 0.3 | 4.2 ± 0.5 |
| total protein | 6.4 ± 0.6 | 6.2 ± 0.6 |

It will be understood that the embodiment described herein is merely exemplary and that a person skilled in the art may make many variations and modifications without departing from the spirit and scope of the invention. All such modifications are intended to be included within the scope of the invention as defined in the appended claims.

I claim:

1. A reagent preparation for the rapid production of serum when said preparation is mixed with a given volume of blood, wherein said mixture includes thrombin in a concentration range of about 0.2–3.0 units per ml, snake venom having a concentration in the range of about 0.005–0.2 mg per ml, and a heparin neutralizing substance including a protamine salt having a concentration in the range of about 0.02–0.08 mg per ml, said preparation causing said blood to rapidly clot to enable one to obtain a serum providing clinically accurate blood chemistry analysis.

2. The reagent preparation according to claim 1, further including a preservative.

3. The reagent preparation according to claim 2, wherein said preservative is selected from the group consisting of sodium azide and thimerosal.

4. The reagent preparation according to claim 1, wherein thrombin is obtained from a bovine source.

5. The reagent preparation according to claim 1, wherein said snake venom is selected from the family of snakes known as the Genus: Agkistrodon, Bothrops, Crotalus, Echis, and Trimeresurus.

6. The reagent preparation according to claim 5, wherein said snake venom is obtained from the snake *Bothrops atrox*.

7. The reagent preparation according to claim 6, wherein said snake venom constitutes the purified procoagulant portion, atroxin.

8. The reagent preparation according to claim 1, wherein said preparation is freeze-dried.

9. The reagent preparation according to claim 1, wherein said mixture contains 0.5 units of thrombin/ml, 0.01 mg snake venom/ml, and 0.05 mg protamine sulfate/ml.

10. The reagent preparation according to claim 3, wherein said preservative is sodium azide having a maximum concentration in said mixture of about 1.0 mg/ml.

11. The reagent preparation according to claim 10, containing 0.5 mg sodium azide/ml.

12. The reagent preparation according to claim 3, wherein said preservative is thimerosal having a maximum concentration in said mixture of about 0.5 mg/ml.

13. The reagent preparation according to claim 12, containing 0.2 mg thimerosal/ml.

14. A cocktail preparation to enable relatively rapid clotting of highly heparinized blood when said cocktail is mixed with a given volume of blood, comprising thrombin, a heparin neutralizing substance, and a snake venom which snake venom is capable of converting fibrinogen to fibrin and is unaffected by the presence of heparin, said thrombin, heparin neutralizing substance, and snake venom present in sufficient amounts to rapidly clot said highly heparinized blood sample and to enable the serum to be separated from said clotted matter, said serum to be chemically tested to provide clinically accurate blood chemistry results.

15. The cocktail preparation according to claim 14, wherein said snake venom is selected from the family of snakes known as the Genus: Agkistroden, Bothrops, Crotalus, Echis, and Trimeresurus.

16. The cocktail preparation according to claim 15, wherein said snake venom is obtained from *Bothrops atrox*.

17. The cocktail preparation according to claim 14, wherein said heparin neutralizing substance is a protamine salt.

18. The cocktail preparation according to claim 17, wherein said mixture includes thrombin having a concentration in the range of about 0.2–3.0 units per ml, snake venom having a concentration in the range of about 0.005–0.2 mg per ml, and protamine sulfate having a concentration in the range of about 0.02–0.08 mg per ml.

19. The cocktail preparation according to claim 18, wherein said mixture contains 0.5 units thrombin/ml, 0.01 mg snake venom/ml, and 0.05 mg protamine sulfate/ml.

20. A method of preparing a cocktail reagent for rapidly producing serum from blood, comprising;
    preparing a first solution by dissolving bovine thrombin in barbital buffered saline to a concentration of 100 units per ml;
    preparing a second solution by dissolving a snake venom in barbital buffered saline to a concentration of 1 mg per ml;
    preparing a third solution by dissolving protamine sulfate in a sodium chloride solution to a concentration of 10 mg per ml; and
    combining a predetermined amount of said first, said second and said third solutions to form a mixture such that the final concentration of said mixture contains 0.5 units thrombin per ml, 0.01 mg snake venom per ml, and 0.05 mg protamine sulfate per ml.

21. The method according to claim 20, wherein said snake venom is selected from the family of snakes known as the Genus: Agkistroden, Bothrops, Crotalus, Echis, and Trimeresurus.

22. The method according to claim 21, wherein said snake venom is obtained from the snake *Bothrops atrox*.

23. The method according to claim 20, further comprising the step of adding a preservative to said first, second, and third solutions such that the concentration of said preservative in each of said solutions is 0.02%.

24. The method according to claim 23, wherein said preservative is selected from the group consisting of sodium azide and thimerosal.

* * * * *